United States Patent [19]

Harris et al.

[11] 4,287,369

[45] Sep. 1, 1981

[54] HYDROFORMYLATION OF ALKENES TO ALDEHYDES

[75] Inventors: Norman Harris; Thomas F. Shevels, both of Stockton-on-Tees, England

[73] Assignee: Davy McKee (Oil & Chemicals) Limited, London, England

[21] Appl. No.: 132,291

[22] Filed: Mar. 20, 1980

[30] Foreign Application Priority Data

Mar. 21, 1979 [GB] United Kingdom ............... 10011/79
Nov. 28, 1979 [EP] European Pat. Off. ......... 79302708.7

[51] Int. Cl.$^3$ ............................................. C07C 45/50
[52] U.S. Cl. ................................................... 568/454
[58] Field of Search ................................. 568/454, 453

[56] References Cited

U.S. PATENT DOCUMENTS

| 3,239,566 | 3/1966 | Slaugh et al. | 568/454 |
| 3,527,809 | 9/1970 | Pruett | 568/454 |
| 3,954,877 | 5/1976 | Gipson | 568/454 |
| 4,148,830 | 4/1979 | Pruett et al. | 568/454 |

FOREIGN PATENT DOCUMENTS

| 2715685 | 10/1977 | Fed. Rep. of Germany | 568/454 |
| 1228201 | 4/1971 | United Kingdom | 568/454 |
| 1298331 | 11/1972 | United Kingdom | 568/454 |
| 1338227 | 11/1973 | United Kingdom . | |
| 1338327 | 11/1973 | United Kingdom . | |
| 1387657 | 3/1975 | United Kingdom | 568/454 |

*Primary Examiner*—Werren B. Lone
*Attorney, Agent, or Firm*—Bernard, Rothwell & Brown

[57] ABSTRACT

A rhodium-catalyzed hydroformylation process in disclosed in which an overhead vapor stream is recovered from the hydroformylation zone containing reactant alkene, hydrogen, carbon monoxide, alkene hydrogenation product(s), aldehyde product and aldehyde condensation products. This vapor stream is subjected to condensation conditions in one or two stages to condense therefrom condensible components comprising unreacted alkene, aldehyde product, and aldehyde condensation products. Non-condensed components of the vapor stream (e.g. $H_2$ and CO) are recycled to the hydroformylation zone. Unreacted alkene is also recycled in liquid form to the hydroformylation zone.

15 Claims, 1 Drawing Figure

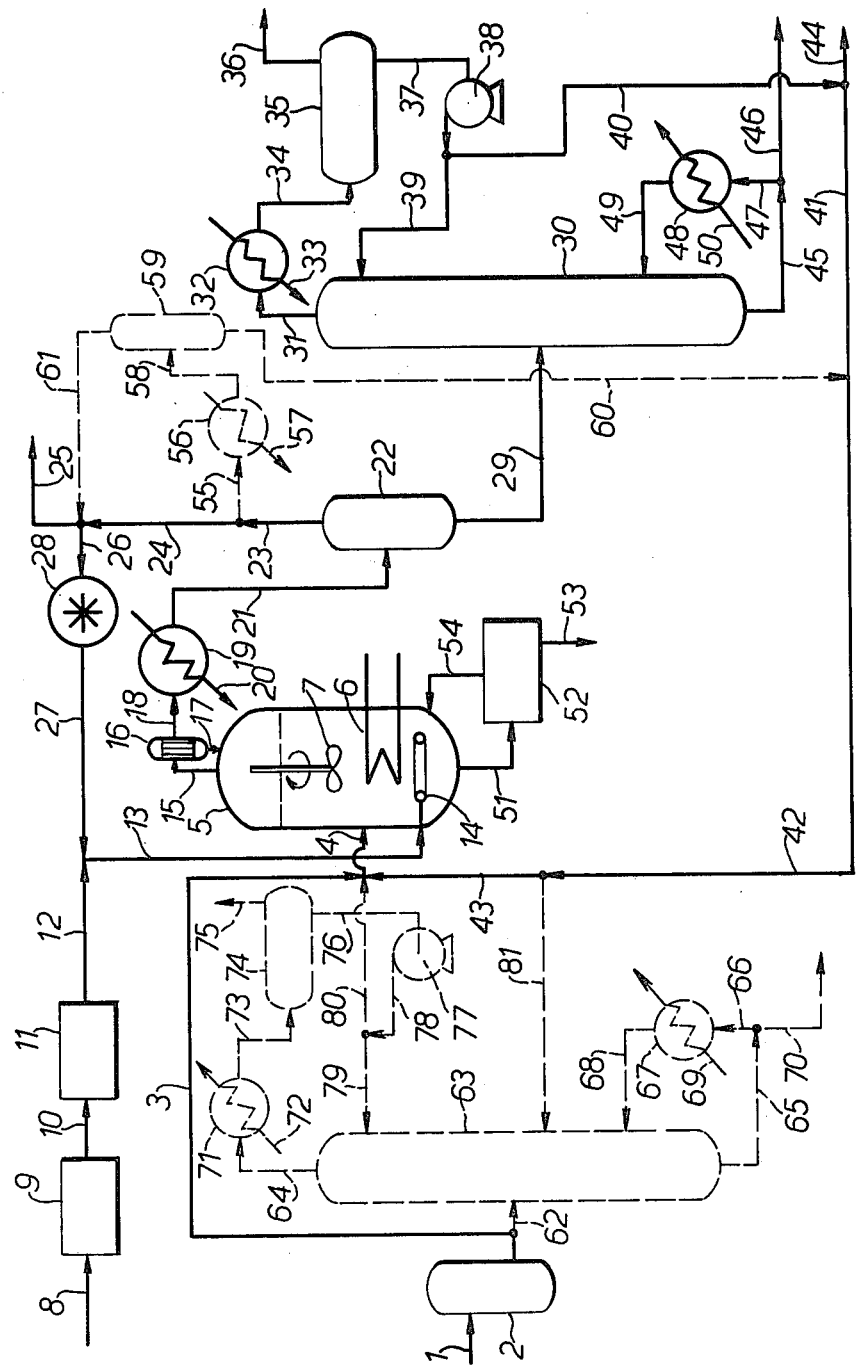

HYDROFORMYLATION OF ALKENES TO ALDEHYDES

This invention relates to a hydroformylation process, more particularly a process for the hydroformylation of an alkene-1 to a corresponding aldehyde product containing one more carbon atom than the starting olefin.

Hydroformylation is a well-known process involving reaction of a mixture of hydrogen and carbon monoxide with the olefinic group of a terminal olefin. Depending on the choice of catalyst, the resulting product may be aldehydic or alcoholic in nature. Although the catalysts originally proposed were based on cobalt, more recently there have been proposed catalysts based on rhodium. Such rhodium based catalysts have the advantage that the pressure of operation is much lower than the pressures necessary when using cobalt catalysts and that product recovery is much simpler than is the case when using a cobalt catalyst. In addition, when utilising propylene or a higher terminal olefin to produce butyraldehyde or the corresponding higher aldehyde, the rhodium catalysts generally permit the attainment of higher n-/iso-product ratios than can be achieved using cobalt catalysts. Since the n-aldehyde usually has a higher value than the iso-aldehyde, this adds to the economic attractions of the rhodium-catalysed processes.

Commercial plants have been built to manufacture propionaldehyde from ethylene and butyraldehyde from propylene utilising a low pressure process involving a rhodium catalyst. An outline of the process is given in "Chemical Engineering", Dec. 5, 1977, pages, 110 to 115. The process is also described in West German Offenlegungsschrift No. 2715685. Further details can be found, for example, in U.S. Pat. No. 3,527,809 and in British Pat. No. 1,338,237.

As described in the afore-mentioned "Chemical Engineering" article the gas-recycle system adopted in the original two plants built for propionaldehyde and butyraldehyde production respectively at Texas City, Tex., U.S.A. and at Ponce, Puerto Rico, involves removal of the product as vapour in an overhead stream taken from the hydroformylation reactor. After air cooling to condense aldehyde product the unreacted gases, including unreacted olefin, are separated from the condensate, compressed and recycled to the hydroformylation reactor. In the butyraldehyde plant in liquid condensate stream contains appreciable amounts of dissolved gases, mainly propylene and propane; these are distilled out in a product stripping column and are recycled as gas to the hydroformylation reactor.

Whilst this gas recycle process is eminently suitable for use in the production of propionaldehyde from ethylene or of butyraldehyde from propylene by hydroformylation, the lesser volatility of the aldehyde product in the case of higher olefins, such as butene-1, requires that a correspondingly higher gas recycle rate must be used in order to remove the aldehyde from the reactor at essentially the same rate as that at which it is formed in order to prevent an increase in volume of the liquid phase in the reactor and an undesirable increase in the proportion of polymeric aldehyde condensation products therein. This in turn requires the use of large recycle gas compressors which are extremely expensive items of equipment and contribute significantly to the costs of installing and operating the plant.

It would be desirable to provide a process for the hydroformylation of alkenes, particularly butene-1 and higher alkenes, whereby the convenient method of product recovery afforded by gas recycle is coupled with use of a relatively small gas recycle compressor.

It is accordingly an object of the invention to provide a process whereby aldehydes can be efficiently and economically produced by hydroformylation of a terminal olefin in the presence of a rhodium complex catalyst utilising a gas recycle method and a gas recycle compressor that is as small as practicable.

According to the present invention there is described a process for the production of an aldehyde by hydroformylation of an alkene in the presence of a rhodium complex catalyst comprising:

providing a hydroformylation zone containing a liquid charge comprising (a) a rhodium complex catalyst wherein rhodium is in complex combination with carbon monoxide and a triorganophosphine, (b) excess triorganophosphine, (c) liquid aldehyde product, and (d) polymeric aldehyde condensation products;

feeding liquid reactant alkene to the hydroformylation zone;

supplying make up hydrogen and carbon monoxide to the hydroformylation zone;

maintaining in the hydroformylation zone temperature and pressure conditions effective for the hydroformylation of the reactant alkene;

recovering from the hydroformylation zone an overhead vapour stream containing reactant alkene, hydrogen, carbon monoxide, alkene hydrogenation product(s), aldehyde product and aldehyde condensation products;

subjecting the vapour stream to condensation conditions to condense therefrom condensible components comprising unreacted alkene, aldehyde product, and aldehyde condensation products;

recycling non-condensed components of the vapour stream comprising hydrogen and carbon monoxide to the hydroformylation zone;

recovering aldehyde product; and recycling unreacted alkene in liquid form to the hydroformylation zone.

The invention is applicable to any alkene capable of undergoing hydroformylation to give an aldehyde that is relatively volatile. There is, however, little advantage in utilising the process in the hydroformylation of ethylene since expensive refrigeration is required in order to liquefy the reactant ethylene and to condense unreacted ethylene from the overhead vapour stream. The process can be applied in the hydroformylation of propylene but experience has shown that the gas recycle process of West German Offenlegungsschrift No. 2715685 is commercially satisfactory. It is thus preferred to utilise $C_4$ or higher alkenes in the process of the invention. For practical purposes octene-1 is probably the highest olefin that can be utilised satisfactorily in the process of the invention. Preferably the olefin comprises butene-1, pentene-1, hexene-1, 2-methyl-butene-1, 3-methyl-butene-1, 2-methyl-pentene-1, 3-methyl-pentene-1, 4-methyl-pentene-1 or 2-ethyl-butene-1.

Although the process of the invention can be practised with an essentially pure alkene-1 feedstock, mixed hydrocarbon fractions containing, in addition to terminal olefins, internal olefins and/or alkanes can also be utilised. The proportion of alkene-1 in such a mixed hydrocarbon fraction may vary within wide limits, for example from about 10 mole % or up to about 90 mole % alkene-1 or more. Typically, however, such a mixed hydrocarbon fraction comprises from about 20 mole % up to about 80 mole % of alkene-1.

The alkene-1 containing feedstock is desirably substantially free from inhibitors, such as dienes (e.g. butadiene), and from catalyst poisons, such as sulphurous compounds and chlorine compounds. A satisfactory procedure for removal of dienes, such as butadiene, comprises hydrofining. Higher sulphurous impurities can be removed to an acceptable level by contact of the feedstock with alumina followed by zinc oxide. Copper-impregnated carbon can be used to reduce the level of chlorinated impurities to a sufficiently low level.

The ratio of hydrogen to carbon monoxide in the make up stream preferably lies in the region of 1:1 by volume. As is well known such $H_2/CO$ mixtures can be produced by conventional synthesis gas plants using hydrocarbon reforming techniques or partial oxidation of hydrocarbons. Experience has shown that metal carbonyls, sulphur compounds and chlorine-containing compounds are undesirable components of the $H_2/CO$ make up stream. Hence it is desirable to submit the make up synthesis gas to purification for the removal of these impurities.

Hydroformylation is effected in the liquid reaction medium in the presence of a catalytically effective amount of the rhodium complex catalyst. Typically the rhodium complex catalyst concentration ranges from about 20 parts per million, calculated as rhodium metal, up to about 1000 parts per million or more. There is no advantage generally in using concentrations of rhodium in excess of about 500 parts per million and usually, on the grounds of expense alone, it will be preferred to operate at a rhodium complex catalyst concentration of not more than about 300 parts per million, calculated as rhodium metal. Typical operating conditions utilise rhodium complex catalyst concentrations of from about 50 parts per million up to about 150 parts per million, calculated as rhodium metal.

The triorganophosphine ligand may be an aliphatic phosphine, such as tributyl phosphine, but is preferably an aromatic phosphine, such as triphenylphosphine, tri-(p-methoxyphenyl)phosphine, trinaphthylphosphine, tritolylphosphine, p-N,N-dimethylaminophenyl diphenylphosphine, and the like. The preferred ligand is triphenylphosphine. During the course of hydroformylation utilising a rhodium complex catalyst small quantities of alkyl diphenylphosphines may be formed by interaction between the triphenylphosphine ligand and the reactant alkene in the presence of the rhodium complex catalyst. Thus, when hydroformylating propylene, for example, small amounts of propyl diphenyl phosphine may be formed as by-product.

The liquid reaction medium contains excess triorganophosphine ligand. Preferably there are at least about 2 moles of free ligand for every gram atom of rhodium present. Usually it will be preferred to operate in the presence of at least 10 moles of free ligand, typically in the presence of at least 75 moles, for example at least 100 moles, of free triorganophosphine ligand per gram atom of rhodium. The upper limit of the amount of free triorganophosphine ligand is not particularly critical and is dictated by the solubility thereof in the liquid reaction medium, as well as by economic and commercial considerations. Although not so expensive as the rhodium inventory, the capital cost of the triphenylphosphine inventory is not an insignificant factor. Under typical operating conditions the free triorganophosphine ligand constitutes from about 2% to about 25% by weight of the liquid reaction medium.

The rhodium complex catalyst may be formed by methods known in the art. For example, hydridocarbonyl tris(triphenylphosphine)rhodium (I) is a crystalline solid and may be introduced into the hydroformylation reactor as such. Alternatively a catalyst precursor, such as rhodium carbonyl triphenylphosphine acetylacetonate or rhodium dicarbonyl acetylacetonate may be introduced into the reactor and the active catalytic species, which has been postulated to be hydridocarbonyl tris(triphenylphosphine)rhodium (I), generated in situ under hydroformylation conditions in the presence of excess triphenylphosphine. Other suitable precursors include $Rh_2O_3$, $Rh_4(CO)_{12}$ and $Rh_6(CO)_{16}$.

The liquid reaction medium further includes aldehyde product and polymeric aldehyde condensation products. The nature of such polymeric condensation products (e.g. dimers, trimers, and tetramers) and a postulated mechanism for their formation are discussed in British Pat. No. 1338237 to which further reference should be made.

The ratio of aldehyde to polymeric aldehyde condensation products in the liquid reaction mixture may vary within wide limits. Typically this ratio lies in the range of from about 1:4 to about 4:1 by weight, e.g. about 1:1 by weight.

In the hydroformylation zone conditions are maintained which are effective for hydroformylation of the reactant alkene. Typically the temperature lies in the range of from about 50° C. up to about 160° C. or more. The temperature should be at least as high as that required to effect hydroformylation but not so high as to destroy the catalyst or to cause undesirable isomerization of terminal olefins to non-terminal olefins. Usually the temperature will lie in the range of from about 70° C. to about 140° C., e.g. in the range of from about 90° C. to about 130° C.

The total pressure in the hydroformylation zone will usually be about 50 kg/cm$^2$ absolute or less and is preferably less than about 20 kg/cm$^2$ absolute. Typically the partial pressure attributable to the olefin is less than about 4.0 kg/cm$^2$ absolute and is preferably less than about 1.5 kg/cm$^2$ absolute. The total partial pressure attributable to hydrogen and carbon monoxide is typically less than about 10 kg/cm$^2$ absolute. Usually the carbon monoxide partial pressure ranges from about 0.1 kg/cm$^2$ absolute to about 1.5 kg/cm$^2$ absolute whilst the hydrogen partial pressure preferably lies in the range of from about 1.5 kg/cm$^2$ absolute to about 7.5 kg/cm$^2$ absolute.

The overhead vapour stream from the hydroformylation zone is subjected to condensation conditions to condense therefrom condensible components comprising unreacted alkene, aldehyde product, and aldehyde condensation products. In one procedure condensation is effected in a single stage so that there is obtained a mixture of condensed alkene, aldehyde product and aldehyde condensation products. Condensation is generally effected by cooling the vapour stream. Depending on the pressure of the vapour stream cooling may be achieved by air cooling, by external cooling against cooling water, or by refrigeration. The resulting condensed mixture may then be distilled to separate unreacted alkene, which appears overhead, from aldehyde product and aldehyde condensation products, which appear as a bottoms product. The resulting aldehyde product-rich bottoms product may then be further purified, e.g. by redistillation in order to separate aldehydes from aldehyde condensation products, and possibly also to separate n-aldehyde from iso-aldehyde. The overhead product from the first-mentioned distillation step is cooled by air cooling, by external water cooling or by refrigeration as appropriate, in order to condense unreacted alkene for return to the hydroformylation zone.

In an alternative procedure the vapour stream from the hydroformylation zone is subjected to a two stage condensation procedure by cooling in two stages. In the first stage an aldehyde-rich condensate is obtained, containing also aldehyde condensation products, whilst unreacted alkene(s) pass(es) on still in vapour form to be condensed in the second stage. In this case the aldehyde-rich condensate can be further worked up, for example as described above by distillation and re-distillation, whilst second stage condensate containing most of the unreacted alkene is cycled to the hydroformylation zone.

In the process of the invention noncondensed components of the vapour stream from the hydroformylation zone are recycled to the hydroformylation zone. It will usually be preferred to conduct the process so that the rate of recycle of such noncondensed components to the hydroformylation zone is at least sufficient to remove aldehyde product in the vapour stream as fast as it is formed. Preferably a gas cycle rate is chosen that is at least sufficient to remove also aldehyde condensation products in the vapour stream as fast as they are produced. In this way build up of liquid in the hydroformylation zone can be prevented. In operation, control of the volume of liquid in the hydroformylation zone can be achieved by appropriate choice of temperature, pressure and gas recycle rate, and by recycle of one or more of the condensed components of the vapour stream (e.g. unreacted alkene, aldehyde product and/or aldehyde condensation products) to the hydroformylation zone.

To prevent build up in the system of inert materials introduced with the reactants or formed as by-products in the process (e.g. alkene hydrogenation product(s)) purge streams may be taken. Thus a purge stream may be taken of the non-condensed components of the vapour stream in order to limit the quantity of, for example, nitrogen in the reaction system. In the process of the invention the hydroformylation conditions may be chosen so that essentially only terminal olefins are hydroformylated whilst nonterminal olefins pass unchanged through the hydroformylation zone and hence behave as inert materials. Hence it will usually be desirable to purge also a part of the unreacted alkene-containing stream in order to limit the amount of non-terminal olefins, as well as paraffin(s) formed as hydrogenation by-product(s), in the system. If the alkene feed stream to the plant is a mixed olefin feedstock, e.g. a mixed butenes feedstock, a preenrichment column can be used in order to separate by distillation an alkene-1 rich overhead fraction from a bottoms product containing olefins that are inert towards the rhodium complex hydroformylation catalyst employed. In this case a part of the unreacted alkene-containing stream can be returned to this preenrichment column so that non-terminal olefins and hydrogenation product(s) are purged as part of the bottoms product therefrom.

In order that the invention may be clearly understood and readily carried into effect a preferred hydroformylation process according to the invention will now be described by way of example only, with reference to the accompanying drawing which is a diagrammatic flow sheet of a plant for the production of n-valeraldehyde from a butene-1 containing feed stream and of a modification thereof.

Referring to the drawing a mixed $C_4$ hydrocarbon liquid feed stream is passed by line 1 to a pretreatment zone 2 in which it is freed from light sulphurous impurities such as $H_2S$, COS and methyl mercaptan by passage in turn through beds of active $Al_2O_3$ and ZnO and also from chlorine-containing impurities by subsequent passage through a bed of copper-impregnated carbon (Girdler G32J catalyst, obtainable from Girdler Chemicals Inc., of Louisville, Ky., U.S.A.). In passing through the bed of active $Al_2O_3$ any COS present is hydrolysed to $H_2S$ due to the presence of traces of water in the feed stream; the active $Al_2O_3$ bed also serves partially to remove $H_2S$ and methyl mercaptan ($CH_3SH$). The ZnO bed then removes any remaining $H_2S$ and $CH_3SH$. Particularly if the feed stream contains traces of molecular oxygen (for example by reason of a previous metal carbonyl removal step) some conversion of methyl mercaptan to dimethyl sulphide ($CH_3SCH_3$) may also occur.

The $C_4$ hydrocarbon liquid feed stream passes on through lines 3 and 4 to a hydroformylation reactor 5.

Hydroformylation reactor 5 contains a catalytic amount of a rhodium-containing hydroformylation catalyst comprising rhodium complexed with carbon monoxide and triphenylphosphine dissolved in a liquid phase containing, in addition to product n-valeraldehyde, polymeric aldehyde condensation products such as trimers. The catalytic species has been postulated to be hydridocarbonyl tris(triphenylphosphine)rhodium (I), which has the formula $HRh(CO)(PPh_3)_3$, and can be generated in situ during the hydroformylation reaction from a suitable catalyst precursor, such as (2,4-pentandionato)dicarbonyl rhodium (I), i.e. the rhodium dicarbonyl complex formed with acetylacetone, or rhodium carbonyl triphenylphosphine acetylacetonate. A description of such a hydroformylation catalyst can be found, for example, in U.S. Pat. No. 3,527,809. The use of aldehyde condensation products as a solvent for the rhodium complex catalyst is described in British Pat. No. 1,338,327. In addition to the rhodium complex catalyst the liquid phase in the hydroformylation reactor 5 also contains an excess of triphenyl phosphine. The mole ratio of triphenyl phosphine:rhodium is approximately 375:1.

The temperature in reactor 5 is maintained at 110° C. by circulating cooling water or steam, as appropriate through coil 6. An impeller 7 rotated by a suitable motor (not shown) is provided in order to mix thoroughly the contents of the hydroformylation reactor 5.

A hydrocarbon feedstock, such as natural gas, naphtha or a gas oil, is supplied through line 8 to a synthesis gas plant 9 (for example a partial oxidation plant or a steam reforming plant). An approximately 1:1 $H_2$:CO mixture passes on from plant 9 through line 10 to a purification section 11 in which the synthesis gas is freed from impurities such as carbonyls, sulphurous compounds and chlorinated compounds. The purified synthesis gas is then fed through lines 12 and 13 to a sparger 14 in hydroformylation reactor 5.

A vaporous stream is removed from hydroformylation reactor 5 overhead through line 15. After passage through a demister 16 which is provided with a return line 17 to reactor 5 for condensed liquid, this stream passes on through line 18 to condenser 19 and is cooled therein to 66° C. by means of cooling water supplied through line 20. The resulting gas/condensate mixture is supplied through line 21 to a product separator 22 from which a gaseous mixture is removed via line 23. The gaseous mixture flows on through line 24. A part thereof is purged through line 25, whilst the remainder is recycled via lines 26, 27 and 13 to hydroformylation reactor 5 by means of recycle compressor 28. The rate of gas recycle through line 27 is sufficiently high, in relation to the temperature and pressure conditions prevailing in reactor 5, to remove product n-valeraldehyde in the vapour stream in line 18 at the rate at which it is formed in reactor 5.

The liquid condensate is removed from product separator 22 through line 29 and fed to a distillation column 30 which contains 20 trays; its working temperature is 193° C.

A gas stream, consisting essentially of unreacted butene-1, cis- and trans-butene-2 and saturated $C_4$ alkanes, is removed overhead via line 31 and is cooled to a temperature of 85.6° C. in condenser 32 which is supplied with cooling water through line 33. The resulting liquid hydrocarbons are then fed via line 34 to reflux drum 35. A gas purge is withdrawn line through 36.

The liquid butenes-containing stream is pumped from reflux drum 35 through line 37 by means of pump 38; of this stream a part is returned to column 30 through line 39, whilst the remainder is supplied to line 40. A major part of the liquid butenes-containing stream in line 40 is returned to hydroformylation reactor 5 through lines 41, 42, 43 and 4, whilst a purge stream is removed from the system through line 44.

A bottoms product, consisting essentially of n-valeraldehyde product and containing a minor proportion of iso-valeraldehyde is withdrawn from column 30 through line 45. Part of this bottoms product is passed to line 46 for purification (e.g. redistillation) and/or further processing and/or storage. The remainder of this bottoms product is recycled through line 47, reboiler 48 and line 49 to column 30. Reboiler 48 is heated by means of steam supplied through line 50.

In order to prevent build-up of "heavies" in the solution in the hydroformylation reactor 5 a bleed stream is removed via line 51 and passed to a regeneration section 52. "Heavies", e.g. valeraldehyde tetramers of a formula analogous to formulae (VI) and (VII) of British Patent Specification No. 1338237, and triphenylphosphine oxide are removed through line 53. (Triphenylphosphine oxide may be formed due to the presence of traces of oxygen in one of the feed streams to the hydroformylation reactor 5). Regenerated solution is recycled to hydroformylation reactor 5 through line 54.

If desired "heavies" removal zone 52 can be dispensed with. Instead spent reactor solution can be withdrawn from the reactor 5 via line 51 and passed to storage, the rate of withdrawal being sufficient to prevent build-up of "heavies" in the reactor 5. At the same time fresh catalyst or catalyst precursor is added via line 54 at a rate sufficient to maintain the rhodium concentration at approximately the chosen level. Such fresh catalyst can be dissolved in an appropriate volume of liquid aldehyde product together with a corresponding amount of free triphenylphosphine. The stored spent catalyst solution can be treated for the recovery of triphenyl phosphine and rhodium from which fresh catalyst or catalyst precursor can be manufactured.

A typical method of "heavies" removal in zone 52 involves extraction of the bleed stream in line 51 in a conventional mixer-settler, after cooling to ambient temperature and depressurising, with phosphoric acid or with an aqueous solution of phosphoric acid containing at least about 40% by weight, and preferably at least about 60% by weight, of orthophosphoric acid. This phosphoric acid extract, which contains essentially all the active rhodium catalyst and free triphenylphosphine, is then neutralised in the presence of a suitable organic hydrophobic solvent, e.g. n-valeraldehyde trimer, and the resulting organic phase recycled to reactor 5 through line 54 after drying. The organic residue from the phosphoric acid extraction step, on the other hand, is passed to storage via line 53; this organic residue contains catalytically inactive rhodium and triphenylphosphine oxide, as well as high boiling n-valeraldehyde condensation products. Such catalytically inactive rhodium may be present due to traces of catalyst poisons in the feed streams to the reactor 5.

As thus described condensation is effected from the vapour stream from reactor 5 in a single stage, i.e. condenser 19. It is alternatively possible to effect condensation in two stages. In this case condenser 19 is operated at a somewhat higher temperature so that unreacted alkene passes on uncondensed in line 21 to product separator 22. Non-condensed components of the vapour stream pass on via line 23 are taken via line 55 to a second stage condensation zone 56 in which unreacted alkene is condensed. Cooling water is supplied to second stage condensation zone 56 through line 57. A gas/liquid mixture passes on through line 58 to a further product separator 59 from which a liquid butenes-rich fraction is withdrawn through line 60 for recycling to the hydroformylation reactor 5 through lines 42, 43 and 4. Uncondensed gases pass on through line 61 to line 26 for recycle to the reactor 5. There is no flow in line 24 in this modification of the plant.

If desired the $C_4$ hydrocarbon feed stream can be subjected to a pre-enrichment step so as to boost the proportion of butene-1 in the feed stream to the reactor 5. This purified $C_4$ hydrocarbons can be passed through line 62 to a splitter column 63 instead of passing on directly via line 3 to reactor 5. Column 63 contains 108 trays. A butene-1 rich stream is removed overhead through line 64, whilst a bottoms product rich in butene-2 is removed through line 65 and is recirculated through line 66 to reboiler 67 before being returned to splitter column 63 through line 68. Reboiler 67 is heated with steam supplied through line 69. A liquid purge, which is rich in cis-and trans-butene-2 and also contains any high boiling sulphurous impurities such as dimethyl sulphide, is removed through line 70.

The butene-1 rich stream in line 64 is passed through condenser 71 which is supplied with cooling water through line 72. The resulting liquid condensate passes on through line 73 to reflux drum 74. Drum 74 is provided with a vent line 75. The liquid butene-1 rich liquid stream is pumped from drum 74 through line 76 by means of pump 77 and on through line 78. Part of this stream is returned to splitter column 63 through line 79, whilst the remainder passes on via lines 80 and 4 to hydroformylation reactor 5.

When a pre-enrichment step is incorporated in the process of the invention, line 44 can be dispensed with. Instead a part of the butene-1 containing liquid stream in line 42 can be passed to column 63 via line 81. In this case the purged materials, which would otherwise have been removed from the system in line 44, are removed in line 70.

The invention is further illustrated with reference to the following Example.

EXAMPLE

Utilising the plant illustrated in full lines in the drawing, a mixed $C_4$ hydrocarbon liquid feed stream is supplied via line 1 to the pretreatment zone 2.

The compositions (in mole %), flow rates, temperatures, and pressures in various of the important lines in the plant are set out below in Table 1.

TABLE 1

| Component | Line 1 | Line 12 | Line 25 | Line 36 | Line 44 | Line 46 |
|---|---|---|---|---|---|---|
| Hydrogen | | 49.96 | 22.31 | 30.54 | | |
| Carbon monoxide | | 47.97 | 7.40 | 16.83 | | |
| Butene-1 | 69.88 | | 8.58 | | 17.53 | 0.42 |
| n-valeraldehyde | | | 1.20 | | 0.60 | 92.20 |
| i-valeraldehyde | | | 0.06 | | 0.17 | 3.60 |
| trans-butene-2 | 15.10 | | 17.05 | | 40.47 | 1.48 |
| cis-butene-2 | 10.06 | | 10.48 | | 26.72 | 1.22 |
| Propane | 0.13 | | 0.35 | | 0.30 | |
| Pentane | 0.54 | | 0.11 | | 0.37 | 0.65 |
| n-butane | 2.23 | | 3.69 | | 8.67 | 0.33 |
| i-butane | 1.06 | | 1.50 | | 2.66 | 0.04 |
| iso-butylene | 1.00 | | 1.27 | | 2.51 | 0.06 |
| Nitrogen | | 2.07 | 26.00 | 52.63 | | |
| "Heavies" | | | | | | Trace |
| Flow rate kg/moles/hr | 300.89 | 379.62 | 20.78 | 4.66 | 105.18 | 185.34 |
| Temperature °C. | 15.55 | 176.67 | 60.56 | 79.44 | 79.44 | 191.67 |
| Pressure kg/cm² | 8.75 | 11.04 | 10.69 | 10.19 | | 10.55 |

Other significant flow rates are set out below in Table 2:

TABLE 2

| Line | 4 | 13 | 18 | 24 | 26 | 29 | 39 | 41 | 53 |
|---|---|---|---|---|---|---|---|---|---|
| Flow rate kg/moles/hr | 527.58 | 2421.65 | 2584.69 | 2062.81 | 2042.03 | 521.88 | 112.17 | 226.69 | 0.38 |

The overall conversion of butene-1 to n- and i-valeraldehydes is 84.4%. The n-/iso-aldehyde ratio is 25.6:1. The resulting aldehyde product can be subjected without further purification to conventional aldolization, dehydration and reduction to yield an acceptable $C_{10}$-plasticiser alcohol consisting predominantly of 2-propylheptanol.

The stream in line 44 is rich in butene-2 and can be used, for example, in the production of butylate petroleum or methyl ethyl ketone.

It will be appreciated by those skilled in the art that, since the butenes are recycled in the liquid phase to the hydroformylation reactor in the form of plant illustrated in the drawing, the gas recycle compressor can be considerably smaller than would be the case if the unreacted butenes were recycled in the gas phase.

We claim:

1. A process for the production of an aldehyde by hydroformylation of an alkene in the presence of a rhodium complex catalyst comprising:
   providing a hydroformylation zone containing a liquid charge comprising (a) a rhodium complex catalyst wherein rhodium is in complex combination with carbon monoxide and a triorganophosphine, (b) excess triorganophosphine, (c) liquid aldehyde product, and (d) polymeric aldehyde condensation products;
   feeding liquid reactant alkene to the hydroformylation zone;
   supplying make up hydrogen and carbon monoxide to the hydroformylation zone;
   maintaining in the hydroformylation zone temperature and pressure conditions effective for the hydroformylation of the reactant alkene;
   recovering from the hydrofromylation zone an overhead vapour stream containing reactant alkene, hydrogen, carbon monoxide, alkene hydrogenation product(s), aldehyde product and aldehyde condensation products;
   subjecting the vapour stream to condensation conditions to condense therefrom condensible components comprising unreacted alkene, aldehyde product, and aldehyde condensation products;
   recycling non-condensed components of the vapour stream comprising hydrogen and carbon monoxide to the hydroformylation zone;
   recovering aldehyde product; and
   recycling unreacted alkene in liquid form to the hydroformylation zone.

2. A process according to claim 1, in which the vapour stream from the hydroformylation zone is cooled to effect condensation of a mixture of the condensible components which is then distilled in a distillation zone to separate an overhead product comprising unreacted alkene from a bottoms product comprising aldehyde product and aldehyde.

3. A process according to claim 2, in which the overhead product from the distillation zone is cooled by air cooling, by external water cooling, or by refrigeration in order to condense unreacted alkene for return to the hydroformylation zone.

4. A process according to claim 1, in which the vapour stream from the hydroformylation zone is cooled to produce an aldehyde-rich condensate containing also aldehyde condensation products, whereupon the uncondensed components comprising unreacted alkene(s) are further cooled to condense unreacted alkene(s) therefrom for recycle to the hydroformylation zone.

5. A process according to claims 1, 2, 3, or 4, in which the rate of recycle of non-condensed components of the vapour stream to the hydroformylation zone is at least sufficient to remove aldehyde product in the vapour stream as fast as it is formed.

6. A process according to claim 5, in which the gas cycle rate is at least sufficient to remove aldehyde condensation products in the vapour stream as fast as they are produced.

7. A process according to claim 6, in which the triorganophosphine is triphenylphosphine.

8. A process according to claim 7, in which the temperature in the hydroformylation zone ranges from about 70° C. to about 140° C.

9. A process according to claim 8, in which the total pressure in the hydroformylation zone is less than about 20 kg/cm² absolute, the partial pressure attributable to the olefin is less than about 1.5 kg/cm² absolute, the total partial pressure attributable to hydrogen and carbon monoxide is less than about 10 kg/cm$^2$ absolute, the partial pressure attributable to carbon monoxide ranges from about 0.1 kg/cm$^2$ absolute to about 1.5 kg/cm$^2$ absolute and the partial pressure attributable to hydrogen ranges from about 1.5 kg/cm$^2$ absolute to about 7.5 kg/cm$^2$ absolute.

10. A process according to claim 9, in which the alkene comprises butene-1.

11. A process according to claim 1, 2, 3 or 4, in which the triorganophosphine is triphenylphosphine.

12. A process according to claim 1, 2, 3 or 4, in which the temperature in the hydroformylation zone ranges from about 70° C. to about 140° C.

13. A process according to claim 1, 2, 3 or 4, in which the total pressure in the hydroformylation zone is less than about 20 kg/cm$^2$ absolute, the partial pressure attributable to the olefin is less than about 1.5 kg/cm$^2$ absolute, the total partial pressure attributable to hydrogen and carbon monoxide is less than about 10 kg/cm$^2$ absolute, the partial pressure attributable to carbon monoxide ranges from about 0.1 kg/cm$^2$ absolute to about 1.5 kg/cm$^2$ absolute and the partial pressure attributable to hydrogen ranges from about 1.5 kg/cm$^2$ absolute to about 7.5 kg/cm$^2$ absolute.

14. A process according to claim 1, 2, 3 or 4, in which the alkene comprises butene-1.

15. A process according to claim 1, 2, 3 or 4, wherein:
(a) the triorganophosphine is triphenylphosphine;
(b) the temperature in the hydroformylation zone ranges from about 70° C. to about 140° C.;
(c) the total pressure in the hydroformylation zone is less than about 20 kg/cm$^2$ absolute, the partial pressure attributable to the olefin is less than about 1.5 kg/cm$^2$ absolute, the total partial pressure attributable to hydrogen and carbon monoxide is less than about 10 kg/cm$^2$ absolute, the partial pressure attributable to carbon monoxide ranges from about 0.1 kg/cm$^2$ absolute to about 1.5 kg/cm$^2$ absolute and the partial pressure attributable to hydrogen ranges from about 1.5 kg/cm$^2$ absolute to about 7.5 kg/cm$^2$ absolute; and
(d) the alkene comprises butene-1.

* * * * *

UNITED STATES PATENT AND TRADEMARK OFFICE
CERTIFICATE OF CORRECTION

PATENT NO. : 4,287,369

DATED : September 1, 1981

INVENTOR(S) : Norman Harris et al.

It is certified that error appears in the above-identified patent and that said Letters Patent are hereby corrected as shown below:

In the first line of the Abstract column, the word "in" should be --is--.

Column 7, line 23, "line through 36." should read --through line 36.--.

Signed and Sealed this

Twenty-ninth Day of December 1981

[SEAL]

Attest:

GERALD J. MOSSINGHOFF

Attesting Officer

Commissioner of Patents and Trademarks